United States Patent
Tooren et al.

(10) Patent No.: US 11,801,325 B2
(45) Date of Patent: Oct. 31, 2023

(54) TISSUE-ADHESIVE POLYMERS

(71) Applicant: Polyganics IP B.V., Groningen (NL)

(72) Inventors: Martin Franke Tooren, Bedum (NL); Justin Van Der Veen, Marum (NL); Dirk Erik Muller, Assen (NL)

(73) Assignee: Polyganics IP B.V., Groningen (NL)

( * ) Notice: Subject to any disclaimer, the term of this patent is extended or adjusted under 35 U.S.C. 154(b) by 341 days.

(21) Appl. No.: 16/651,431

(22) PCT Filed: Oct. 1, 2018

(86) PCT No.: PCT/NL2018/050650
§ 371 (c)(1),
(2) Date: Mar. 27, 2020

(87) PCT Pub. No.: WO2019/066658
PCT Pub. Date: Apr. 4, 2019

(65) Prior Publication Data
US 2020/0282103 A1    Sep. 10, 2020

(30) Foreign Application Priority Data
Sep. 29, 2017 (NL) ..................................... 2019650

(51) Int. Cl.
*A61L 24/04* (2006.01)
*C08L 71/02* (2006.01)

(52) U.S. Cl.
CPC ............. *A61L 24/046* (2013.01); *C08L 71/02* (2013.01)

(58) Field of Classification Search
CPC ................................ A61L 24/046; C08L 71/02
USPC ......................................................... 156/327
See application file for complete search history.

(56) References Cited

U.S. PATENT DOCUMENTS

| 5,122,614 A | 6/1992 | Zalipsky |
| 5,583,114 A | 12/1996 | Barrows et al. |
| 6,312,725 B1 | 11/2001 | Wallace et al. |
| 11,160,900 B2 * | 11/2021 | Tooren ................ A61L 24/0042 |
| 2004/0096507 A1 | 5/2004 | Kwang et al. |

FOREIGN PATENT DOCUMENTS

| CN | 101035572 A | | 9/2007 |
| CN | 101724144 A | | 6/2010 |
| CN | 104877127 | * | 9/2015 |
| CN | 3315531 | * | 5/2018 |
| EP | 2360203 A1 | | 8/2011 |
| WO | 9603159 A1 | | 2/1996 |
| WO | 2006042161 A2 | | 4/2006 |
| WO | 2008019383 A2 | | 2/2008 |
| WO | 2009132153 A2 | | 10/2009 |

OTHER PUBLICATIONS

Ellis et al. "The ideal tissue adhesive in facial plastic and reconstruct surgery". J Otolaryngol., 19, pp. 68-72, 1990 (abstract).

* cited by examiner

*Primary Examiner* — Yih-Horng Shiao
(74) *Attorney, Agent, or Firm* — Banner & Witcoff, Ltd.

(57) ABSTRACT

The invention is directed to a multi-arm tissue-adhesive polymer wherein at least six or more arms each comprise a reactive functional group that can form a urethane or a urea bond with an amine group present in tissue, as well as to the use thereof for sealing or closing of tissue and use in a medical treatment of a human or animal body. In a further aspect, the invention is directed to a method for the preparation of said multi-arm tissue-adhesive polymer.

20 Claims, 2 Drawing Sheets

TISSUE-ADHESIVE POLYMERS

RELATED APPLICATIONS

This application is a National Stage Application under 35 U.S.C. 371 of co-pending PCT application PCT/NL2018/050650 designating the United States and filed Oct. 1, 2018; which claims the benefit of NL application number 2019650 and filed Sep. 29, 2017 each of which are hereby incorporated by reference in their entireties.

The invention is in the field of biomedical polymers. The invention is in particular directed to tissue-adhesive polymers.

Tissue-adhesive polymers are typically used in medical devices, for instance foams or sheets, to enable adhesion of the medical devices to tissue of humans or animals. The medical device may be used to seal and/or close wounds in human or animal patients.

Examples of conventional tissue-adhesive polymers include polymers functionalized with activated esters such as N-hydroxysuccinimide (NHS) esters. It is generally believed that these polymers can react with amine groups of the tissue to form covalent amide bonds between the tissue and the polymers and that this reactivity provides the tissue-adhesive properties.

A specific example of a conventional tissue-adhesive polymer is the 4-arm succinimidyl glutarate terminated poly(ethylene oxide) having an average molecular weight $M_n$ of 10.000 (CAS number 154467-38-6, also referred to as 4-arm-PEG10k-SG) as represented by the formula:

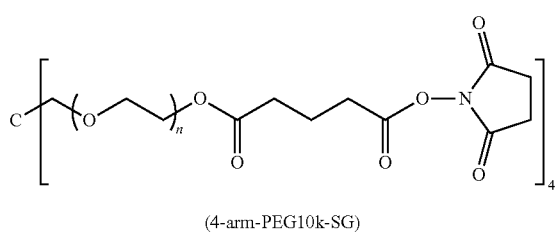

(4-arm-PEG10k-SG)

Drawbacks of the 4-arm-PEG10k-SG is that the amide bond formed with the tissue and the presence of the ester bond results in a relatively weak tissue-adhesion, in particular at the long term.

In general, it is desired that the adhesive-strength between the polymers and the tissues is large, in particular at the long term (i.e. several days to weeks) Accordingly, the present invention is directed to provide a tissue-adhesive polymer that provides an improved adhesive-strength.

The present inventors surprisingly found that an improved tissue adhesive strength can be obtained with a multi-arm polymer wherein at least six or more arms each comprise a reactive functional group that can form a urethane, a thiourethane or a urea bond with an amine group present in tissue. The reactive functional group is herein accordingly also referred to as the tissue-reactive group.

Tissue-adhesive properties can be expressed as the gel time with polyamine polymers such as polyethyleneimine and/or adhesion on tissue such as collagen, dura mater or liver tissue. In this respect, reference is made to the examples provided below.

Functional groups that are capable of forming a urethane can be represented by the formula X—C(O)-LG, wherein X is an oxygen atom O and LG represents a leaving group. As such, upon formation with tissue (i.e. animal or bodily tissue), the leaving group LG may leave and the tissue-adhesive polymer is covalently bound to the tissue via the O—C(O)—NH, i.e. urethane, bond. Similarly, functional groups that are capable of forming a urea can be represented by the formula X—C(O)-LG, wherein X is a nitrogen atom N and LG represents a leaving group. As such, upon formation with tissue (i.e. animal or bodily tissue), the leaving group LG may leave and the tissue-adhesive polymer is covalently bound to the tissue via the N—C(O)—NH, i.e. urea, bond. Functional groups that are capable of forming a thiourethane can be represented by the formula X—C(O)-LG, wherein X is an sulfur atom S and LG represents a leaving group. As such, upon formation with tissue (i.e. animal or bodily tissue), the leaving group LG may leave and the tissue-adhesive polymer is covalently bound to the tissue via the S—C(O)—NH, i.e. thiourethane, bond.

Accordingly, in a particular embodiment the multi-arm tissue-adhesive polymer is a polymer according to formula I:

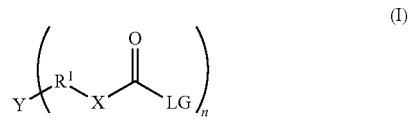

wherein n is an integer of 6 or more; preferably wherein n is in the range of 6-12, more preferably 6-10, even more preferably 7-8, most preferably wherein n is 8;
LG represents a leaving group;
X is selected from S, NH and O;
$R^1$ represents a polymeric group; and
Y represents a core structure;
such that $R^1$—X—C(O)-LG represents each arm comprising the reactive functional group X—C(O)-LG.

The tissue-adhesive polymer can be based on a variety of polymers or polymeric groups. The invention is not necessarily limited to poly(ethylene glycol) like the most commonly used conventional multi-arm polymers are. However, the inventors did find that good reaction with the tissue (i.e. good adhesion) can in particular be obtained if the tissue-adhesive polymer is based on a hydrophilic polymer. Examples of suitable hydrophilic polymers include hydrophilic polyether, polyester, polycarbonates, polyurethanes, polyetherurethanes, polyurethane urea, poly(vinylpyrrolidone), poly(saccharide), poly(vinyl alcohol), polyoxazoline, or combinations thereof. The presence of a hydrophobic polymeric part is not necessarily excluded, as long as this is not detrimental to the adhesive properties of the tissue-adhesive polymer. For instance, the hydrophobic part can be overruled by a hydrophilic part of the tissue-adhesive polymer such that overall the polymer remains adhesive to tissue.

Particularly preferred polymeric groups include polyether, polyester, polycarbonate such as poly(alkylene glycol) or a poly(lactic acid), poly(caprolactone), polydioxanone, poly(glycolide) or a poly(trimethylene carbonate). Although polyesters such as poly(lactic acid) and poly (caprolactone) show favorable hydrophilic properties, the present of the ester bonds in the polymers, in particular when combined with ethers, results in a shorter adhesion than the polyether and polycarbonate. Accordingly, even more preferably the polymer or polymeric group comprises poly (ethylene glycol) (PEG), polycaprolactone (PCL), poly(lactic acid) (PLA), for instance poly(L-lactic acid) (PLLA), a co-polymer of PCL and PLA or a poly(trimethylene carbonate) (PTMC), most preferably PEG.

The reactive functional group comprises a leaving group LG that leaves upon the reaction with an amine. As long as the leaving group is not detrimental to the reactivity of the tissue-adhesive polymer with the tissue, the leaving group is not of a major influence to the adhesive strength because it leaves the polymer and the tissue after reaction. The tackiness of the polymer towards the tissue can however be influence with the choice of the leaving group since the leaving group can influence the reaction rate of the polymer towards the tissue. The reaction rate should not be too low such that the adhesion will practically not occur, but it should neither be too high such that the reactive group will be too prone to a reaction with other components than the tissue such as water. In this respect, it was found that preferably the leaving group LG is an alcohol radical comprising an electron-withdrawing group, preferably an alcohol radical wherein the alcohol is selected from the group consisting of perfluoroalkyl alcohol, p-nitro-phenol, 3,4,5-trichlorophenol, pentafluorophenol, 1-benzotriazolyl alcohol, 1-hydroxy-7-azabenzotriazole, 1-hydroxybenzotriazole, and N-hydroxysuccinimide alcohol and derivatives thereof such as N-hydroxymaleimide, N-hydroxyphthalimide, endo-N-hydroxy-5-norbornene-2,3-dicarboximide and a N-hydroxysulfosuccinimide salt, more preferably wherein the alcohol is a N-hydroxysuccinimide alcohol.

The multi-arm nature of the polymer can be attributed to a core (also referred to as initiator) which has multiple reactive groups to which the arms can be connected. The core or initiator can appropriately be selected based on the polymeric part on which the arms are based. For instance, in the preferred embodiments wherein the polymeric group comprises poly(lactic acid), glycolide, caprolacton, poly(ethylene glycol) and/or a poly(trimethylene carbonate), the core can be based on a polyol such as glycerol (GL), pentaerythritol (P), hexaglycerol (HG), tripentaerytritol (TP), trimethylolpropane (TMP) and dipentaerythritol (DP). As such, in a preferred embodiment, Y of formula I is based on a Y is based on a polyol comprising n hydroxyl groups, preferably wherein Y is based on a polyol of any of structures II, III or IV as depicted below,

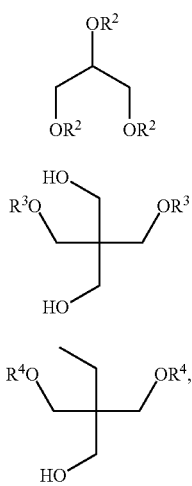

II

III

IV wherein each $R^2$ is individually H or

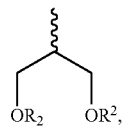

each $R^3$ is individually H or

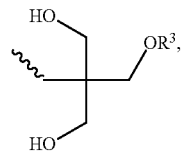

each $R^4$ is H or

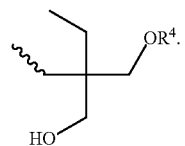

The $R^2$, $R^3$ and $R^4$ can be selected based on the amount of desired hydroxyl groups. For instance, hexaglycerol (HG) can be represented as

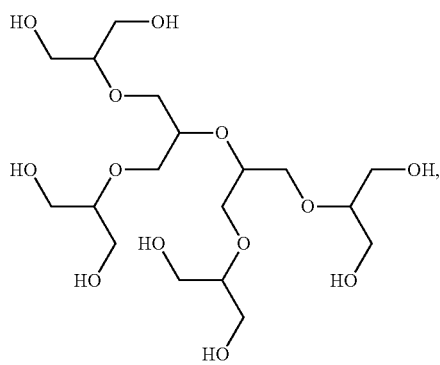 [SMILES: OCC(CO)OCC(COC(CO)CO)OC(COC(CO)CO)COC(CO)CO]

pentaerythritol as formula III, wherein each $R^2$ of formula III is

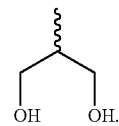

In a particular embodiment, the core is the initiator for the preparation of a multi-arm PEG, which is then used as a subsequent initiator in a polymerization reaction with lactide, trimethylenecarbonate, glycolide of caprolacton to form a multiarm block copolymer comprising a multi-arm PEG segment extended with one or more of these monomers.

It is noted that Y may comprise ($R^1$—X—C(O)-LG) as the sole substituent, but it may also comprise further groups (e.g. non-tissue-reactive groups) such as for instance $R^1$—X—H. Generally, it is preferred that all arms comprise the tissue-reactive group, but it may be that, e.g. due to limitation in the method for preparation (vide infra), not all arms are substituted with the tissue-reactive group. The degree of arms that comprise the tissue-reactive group is herein expressed as the substitution degree. The substitution degree can be determined by 1H-NMR in combination with the following formula $$\text{substitution degree } (\%) = \frac{A}{Q \times R} \times \frac{Z \times M_n}{B \times M_w} \times 100\% \quad \text{(IV)}$$

wherein:
A is the area of the peak or peaks corresponding to all the protons of the leaving group;
Q is the number of protons in leaving group;
R is the total number of arms of the tissue-adhesive polymer;
B is the area of the peak or peaks corresponding to all the protons of polymer arms;
Z is the number of protons in the monomer on which the polymeric group is based;
$M_w$ is the molecular weight of monomer on which the polymeric group is based;
$M_n$ is the number-average molecular weight of the tissue-adhesive polymer without the reactive functional groups.

Good adhesive strengths were obtained when the substitution degree is more than 60%, preferably more than 80% as determined by $^1$H-NMR.

The inventors further surprisingly found that the tissue-adhesive properties of the polymer increase with the number of arms and as well as with the number-average molecular weight ($M_n$) of the polymer. In addition, better adhesion is obtained with an improved length of each arm that comprises the functional reactive group. It is thus not necessarily the case that the total amount of functional reactive groups determines mainly the adhesive strength. In certain embodiments, the adhesive strength can be mainly correlated to the amount of arms comprising the functional reactive groups in combination with the molecular weight. Since from a toxicological point of view, a low amount of function reactive groups is desired, it may be preferred that the amount of functional reactive groups is less than 5%, more preferably less than 4%, most preferably less than 3%, based on the total weight of the tissue-adhesive polymer. These amounts are particular applicable on NHS as the functional reactive group.

The length of the arms can be expressed with their molecular weight. Accordingly, on average, the number-average molecular weight ($M_n$) of each arm is preferably in the range of 500 Da to 50 kDa, more preferably 1-25 kDa, most preferably 2 to 10 kDa. In addition, number-average molecular total weight of the multi-arm tissue-adhesive polymer is preferably in the range of 5 to 100 kDa, more preferably in the range of 10-80 kDa, most preferably in the range of 20-60 kDa. For instance, very good results were obtained with an 8-armed (PEG) having a number-average molecular weight of 40.000 g/mol (i.e. 40 kDa), of which each arm is thus about 5 kDa. The number-average molecular weight can be determined by known analytical techniques such as size exclusion chromatography (SEC) and/or matrix assisted laser desorption ionization time of flight mass spectrometry (MALDI-TOF-MS).

The polymer of the present invention is particularly suitable for application in medical devices such as medical foams and medical sheets. It may further suitably be applied on tissue as a spray to form a tissue cover or sealing in situ.

A further aspect of the present invention is a method for the preparation of the multi-arm tissue-adhesive polymer comprising reacting a polymer compound having the structure Y—$R^1$—XH with a compound having structure of formula III in accordance with the following scheme:

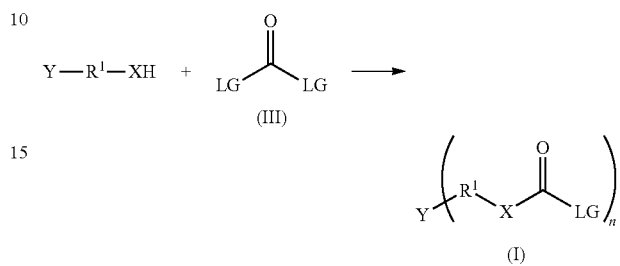

to form the multi-arm tissue-adhesive polymer of formula I.

The polymer compound having the structure Y—$R^1$—XH can be commercially available (such as for instance hydroxyl-terminated 4-arm PEG having a $M_n$ of 10 kDA) or can be easily produced with standard polymer synthesis procedures by initiating polymerization with Y-based initiator.

As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features.

For the purpose of clarity and a concise description features are described herein as part of the same or separate embodiments, however, it will be appreciated that the scope of the invention may include embodiments having combinations of all or some of the features described.

The present invention can be illustrated by the following non-limiting examples.

EXAMPLE 1 PREPARATION OF THE POLYMERS

The synthesis of a succinimidyl carbonate terminated 8-arm PEG having a molecular weight of 40 kDa (8-arm-PEG40k-SC) was carried out in accordance with the following scheme and the procedure below.

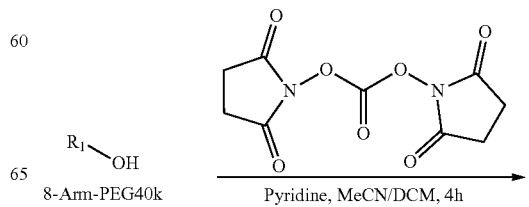

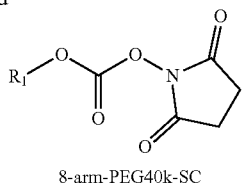

8-arm-PEG40k-SC

Figure 1:
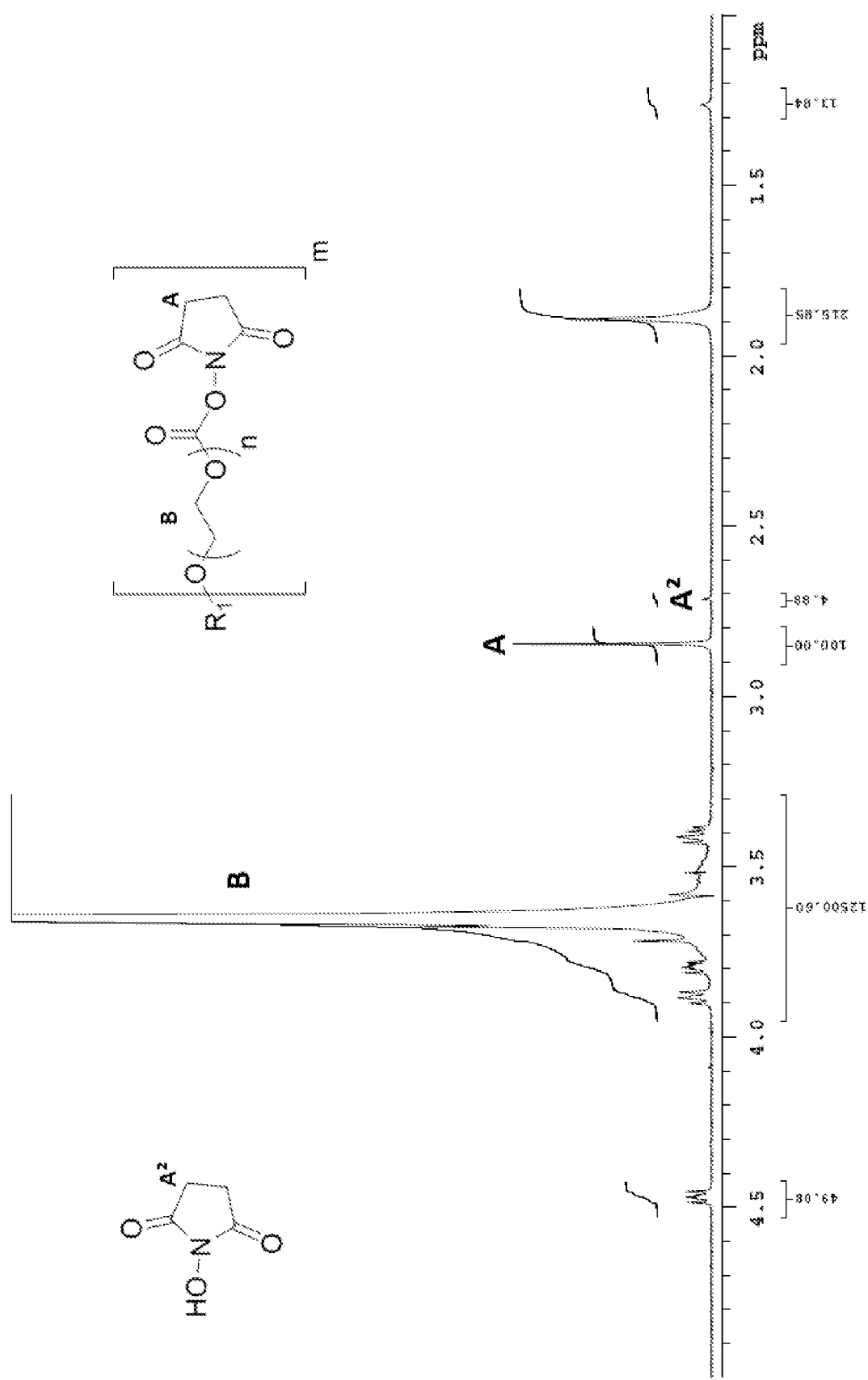
FIG. 1 illustrates the 1H-NMR spectrum.

Disuccinimidylcarbonate (0.03 mmol, 256.17 g/mol, 3 equivalents, 7.69 g) was added with stirring to commercially available 8-Arm-PEG40k-OH (1.25 µmol, 1 equivalent, 50 g) in dichloromethane (100 mL) and acetonitrile (200 mL). Pyridine (5 mL) was added. The reaction mixture was stirred for 4 h and the solvent was removed in vacuo. The residue was dissolved in 450 mL of ethyl acetate with heating (45° C.). An amount of 450 mL of tert-butylmethyl ether (TBME) was added to the mixture and the result was subsequently cooled in a freezer. A white solid (43 g, 83% yield) was formed which was purified by crystallization The substitution degree was determined in accordance with the 1H-NMR spectrum as illustrated in FIG. 1 and formula IV wherein A the area of the peak at about 2.85 ppm, Q is 4, R is 8, B is the area of the peaks in the range of 3.3-3.9 ppm, Z is 4, $M_w$ is 44.05, $M_n$ is 40.000. Six different batches gave a substitution degree in the range of 91-97%. Higher substitution degrees may be obtained by increasing the reaction time, variation in the purification method and/or the equivalents of the succinimidyl carbonate.

This procedure was repeated with the different starting polymer compounds to obtain the corresponding multi-arm tissue-adhesive polymers as provided in Table 1. The nomenclature in Table 1 is constructed follows [number of arms]-[polymeric group] [number-average molecular weight][(core)]-[reactive group]. Thus 8-arm-PEG40k(HG)-SC corresponds to succinimidyl carbonate (SC) terminated 8-arm PEG having a molecular weight of 40 kDa which is based on a hexaglycerol core.

EXAMPLE 2 GEL TIME AND STABILITY

The tissue-adhesion properties were tested in a model system in which the gel time of the polymers with the amine-containing polyethyleneimine was determined. Fast jellification corresponds to a fast reaction with tissue, while slow jellification corresponds to a slower reaction with tissue.

Accordingly, the gel time in polyethyleneimine of some of the polymers prepared in Example 1 were measured as follows.

A solution of 50 mg multiarm tissue adhesive polymer in 1 mL Sorensen buffer solution was added to a solution of 5 mg polyethyleneimine (PEI) in 1 mL Sorensen buffer in a vial. The time until gelation of the solution is measured for 5 times. The results are provided in Table 2.

The fastest jellification is obtained for 8-armPEG40k tissue adhesive polymers 1, 6 and 10

The gel-containing vials with polymers 1-6 were placed in an incubation oven at a temperature of 37° C. Within 24 h, the 8-armPEG40k-SG (polymer nr. 10) was completely dissolved in the Sorensen buffer solution indicating degradation of the adhesive polymer. The other multi-arm tissue adhesive polymers 1-6 remained a gel for at least 1 week. This is indicative for the lasting adhesion to the tissue.

TABLE 2

| Polymer nr. | Gel time in PEI (s) |
|---|---|
| 1 | 9.5 |
| 2 | 130 |
| 3 | 12 |
| 4 | 62 |
| 5 | 46 |
| 6 | 9.3 |
| 10 | 8.8 |

TABLE 1

| Polymer nr. | Starting Polymer Compounds | Multi-Arm Tissue-Adhesive Polymer | Substitution Degree (%) | NHS Amount (wt. %) |
|---|---|---|---|---|
| 1 | 8-arm-PEG40k(HG)-OH | 8-arm-PEG40k(HG)-SC | 91-97 | 1.88 |
| 2 | 4-arm-PEG10k(HG)-OH | 4-arm-PEG10k(HG)-SC[1] | 90 | 3.68 |
| 3 | 4-arm-PEG20k(HG)-OH | 4-arm-PEG20k(HG)-SC[1] | 89 | 1.88 |
| 4 | 6-arm-PEG15k(DP)-OH | 6-arm-PEG15k(DP)-SC | 96 | 3.68 |
| 5 | 8-arm-PEG20k(HG)-OH | 8-arm-PEG20k(HG)-SC | 92 | 3.68 |
| 6 | 8-arm-PEG40k(TP)-OH | 8-arm-PEG40k(TP)-SC | 90 | 1.88 |
| 7 | 8-armPCL40k(HG)-OH | 8-armPCL40k(HG)-SC | 90 | 1.88 |
| 8 | 8-armPLA40k-(HG)OH | 8-armPLA40k(HG)-SC | 90 | 1.88 |
| 9 | 8-arm CL/PLLA40k-OH | 8-armPCL/PLLA40k(HG)-SC | 90 | 1.88 |
| 10 | 8-arm-PEG40l(HG)-OH | 8-arm-PEG40k(HG)-SG[1] | 90 | 1.85 |

[1]comparative examples: 4-arm polymers and 8-arm succinimidyl glutarate terminated poly(ethylene oxide) having an average molecular weight $M_n$ of 40.000 commercially available from JenKem Technology USA.

EXAMPLE 3 PREPARATION OF DEVICES FOR ADHESION TESTS

Foam devices comprising the tissue-adhesive polymers were prepared as follows.

A solution of a polyurethane (4.84 g in 152 mL of 1,4-Dioxane) was prepared and stirred until the polyurethane was entirely dissolved in 1,4-Dioxane (approximately 1 h). When the polyurethane was dissolved, 190 mg of sodium phosphate dibasic ($Na_2HPO_4$) as the buffering agent was added. The mixture was stirred for 1 h. An amount of 1.9 g of the tissue-adhesive polymers prepared according to Example 1 were added. Next, about 12 ml of the prepared solution of the carrier polyurethane was poured on top of the sheet layer inside the mold.

The result was freeze dried to remove the solvents and obtain the device.

Devices were prepared with most of the polymers as provided in Table 1, see Table 3.

EXAMPLE 4 ADHESION ON DURA MATER AND LIVER TISSUE

The adherences (N) of the tissue-adhesive polymers in the devices as prepared in Example 3 on liver and dura mater tissue were determined as follows.

Test articles of the devices were cut in pieces of 20×20 mm and attached to a piston using 2-sided tape. The surface of the liver or dura mater tissue was pre-wetted with saline. The test article was pressed on the liver surface using an Instron tensile tester with a ramp of 20 mm/min until a force of 10 N was reached. After 2 min, the test article was removed from the liver or dura mater surface with 20 mm/min and the force required was measured. The maximum load is reported as being the adherence (N).

The results are provided in Table 3.

TABLE 3

| Device nr. | Polymer nr. | Liver adherence (mbar) | Dura tensile test (N) |
|---|---|---|---|
| 1 | 1 | 1.3 | 5.4 |
| 2 | 2 | 0.2 | 4.4 |
| 3 | 3 | 0.5 | 3.9 |
| 4 | 4 | 0.8 | 3.3 |
| 5 | 5 | 1.1 | 3 |
| 6 | 6 | 1.2 | 6.5 |
| 10 | 10 | 1.0 | 3.6 |

EXAMPLE 5 TISSUE-ADHESIVE PROPERTIES: TENSILE STRENGTH

For the tensile strength determination, a 20×50 mm rectangular piece of collagen, liver and duramater tissue were cut with a surgical blade. Square test articles of the device (sized 20×20 mm) were cut with a surgical blade. The 20×50 mm rectangular piece of collagen was cut exactly in the middle and wetted with demineralized water. A 20×20 mm test article was placed over the cut and pressed for 10 seconds, subsequently 1 kg of pressure was applied for 2 minutes. Paper clamps with additional sanding paper for grip were used to place the collagen including the test article in the clamps of the tensile tester. The tensile strength was determined with a constant cross-head speed of 10 mm $min^{-1}$ and the load extension diagram was recorded. A graph was generated (load vs extension) and the load at yield (zero slope) is determined as the adhesion strength of the test article.

The measurement was performed at 0, 3 and 7 days. For the 3 and 7 day time period, the rectangular pieces of collagen containing the test article is placed in Störensen buffer solution and placed in an incubation oven which was set to a temperature of 37° C. After 3 or 7 days, the tensile strength is determined according to the method described above.

Figure 2:
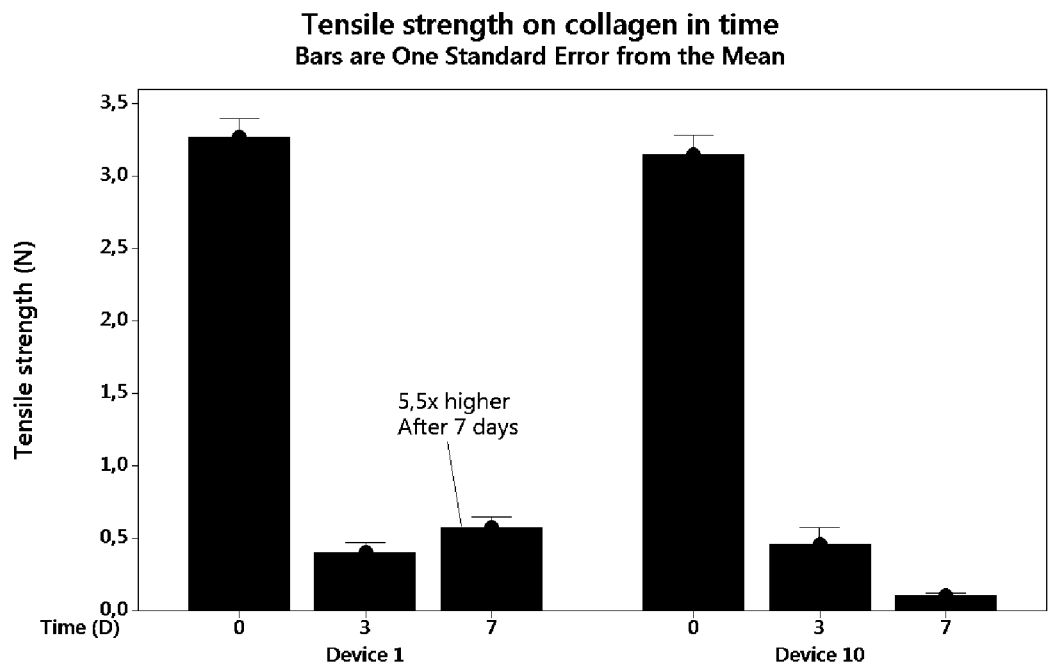
FIG. 2 illustrates Example 5 results.

The results are provided in FIG. 2.

EXAMPLE 6 TISSUE-ADHESIVE PROPERTIES: BURST PRESSURE

The devices as prepared in Example 3 were tested for the burst pressure as an indication of the strength of the adhesion to tissue.

For burst pressure testing, a 30 mm circle was punched in the collagen. At the time of use, a 4 mm biopsy punch was made in the centre of the circle. A Teflon ring was placed on the substrate to centre the defect. A 20 mm circular test sample was placed on the defect (pre-wetted with demineralized water) and a weight of 1 kg was place on top of the device for a period of 2 minutes.

The burst pressure setup has a main unit that comprises a pressure vessel connected to a flow sensor and pressure sensor. The flow sensor feeds in to a test location at which a sample can be placed. By regulating the flow sensor the pressure in the test location can be controlled/build up, thereby making it possible to evaluate what the performance of the sample is in terms of pressure. This pressure was recorded by the aforementioned pressure sensor.

The collagen with the test article was placed onto the fixture base. An O-ring (22 mm ID) was placed on top of the collagen containing the test article and secured by closing with 4 knobs. A water flow rate of 1 mL/min (60 g/h) was applied. During the determination, the maximum pressure was recorded and reported in mbar. The measurement was performed at both 0 days as 7 days. For the 7 day time period, the circular pieces of collagen containing the test article was placed in Sörensen buffer solution and placed in an incubation oven which was set to a temperature of 37° C. After 7 days, the burst pressure was measured according to the method described above.

Figure 3:
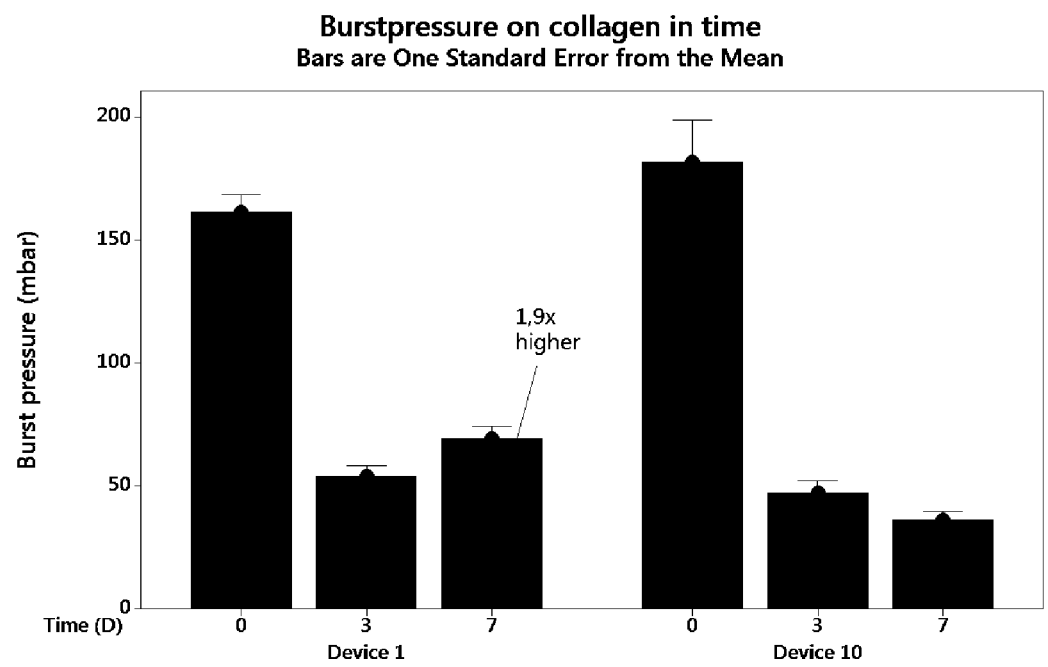
FIG. 3 illustrates Example 6 results.

The results are illustrated in FIG. 3.

The invention claimed is:

1. Multi-arm tissue-adhesive polymer comprising at least six arms, wherein each of the at least six arms comprises a polymeric group and a reactive functional group that can form a thiourethane, a urethane or a urea bond with an amine group present in tissue, wherein the polymer is of formula I

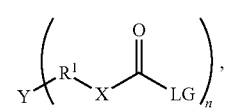

wherein n is an integer of 6 or more;
LG is a leaving group;
X is selected from the group consisting of S, NH and O;
$R^1$ is a polymeric group; and
Y is a core structure;
such that $R^1$—X—C(O)-LG is each arm comprising the reactive functional group X—C(O)-LG; and wherein Y is based on a polyol of any of structures ii, iii and iv

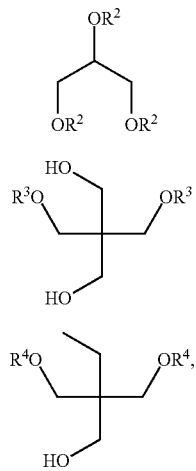

wherein each $R^2$ is individually H or the group for connecting to another structure ii, each $R^3$ is individually H or the group for connecting to another structure iii, and each $R^4$ is individually H or the group for connecting to another structure iv, depending on the desired amount of hydroxyl groups to yield the at least six arms.

2. The multi-arm tissue-adhesive polymer according to claim 1, wherein Y is based on hexaglycerol (HG), tripentaerytritol (TP) or dipentaerythritol (DP).

3. The multi-arm tissue-adhesive polymer according to claim 1, wherein the polymeric group $R^1$ comprises a polyether, polyester, polycarbonates, polyurethanes, polyetherurethanes, polyurethane urea, poly(vinylpyrrolidone), poly(saccharide), poly(vinyl alcohol), or polyoxazoline, or combinations of distinct $R^1$ thereof.

4. The multi-arm tissue-adhesive polymer according to claim 1, wherein the reactive functional group comprises a leaving group LG that is an alcohol radical functioning as an electron-withdrawing group.

5. The multi-arm tissue-adhesive polymer according to claim 1, wherein n is an integer in the range of 6-12.

6. The multi-arm tissue-adhesive polymer according to claim 1, wherein Y is based on a polyol comprising n hydroxyl groups, wherein n is defined above.

7. The multi-arm tissue-adhesive polymer according to claim 1, wherein each arm has a number-average molecular weight in the range of 500 Da to 50 kDa.

8. The multi-arm tissue-adhesive polymer according to claim 1, wherein the polymer has molecular weight in the range of 5 to 100 kDa.

9. The multi-arm tissue-adhesive polymer according to claim 1, wherein the polymer has a substitution degree of the arms with the reactive functional group of more than 60% as determined by $^1$H-NMR.

10. The multi-arm tissue-adhesive polymer according to claim 1, wherein the reactive functional group is present in an amount of less than 5% based on the total weight of the tissue-adhesive polymer.

11. Method for the preparation of the multi-arm tissue-adhesive polymer according to claim 1, comprising reacting a polymer compound having the structure $Y—R^1—XH$ with a compound having structure of formula III,

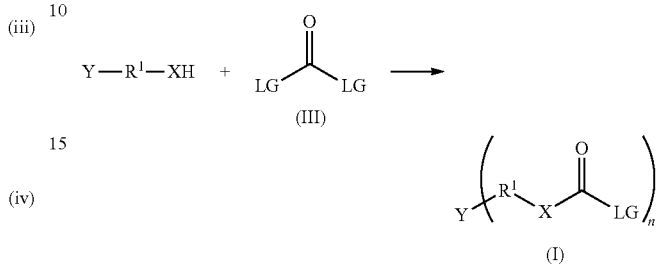

to form the multi-arm tissue-adhesive polymer of formula I.

12. A method of sealing or closing tissue comprising applying the multi-arm tissue-adhesive polymer according to claim 1 to tissue in a manner to seal or close the tissue.

13. Medical foam or sheet comprising the multi-arm tissue-adhesive polymer according to claim 1.

14. The multi-arm tissue-adhesive polymer according to claim 1, wherein the polymeric group $R^1$ comprises poly(alkylene glycol), poly(lactic acid), poly(caprolactone), polydioxanone, poly(glycolide) or poly(trimethylene carbonate).

15. The multi-arm tissue-adhesive polymer according to claim 1, wherein the reactive functional group comprises a leaving group LG that is an alcohol radical, wherein the alcohol is selected from the group consisting of perfluoroalkyl alcohol, p-nitro-phenol, 3,4,5-trichlorophenol, pentafluorophenol, 1-benzotriazolyl alcohol, 1-hydroxy-7-azabenzotriazole, 1-hydroxybenzotriazole, and N-hydroxysuccinimide alcohol or derivatives thereof.

16. The multi-arm tissue-adhesive polymer according to claim 1, wherein the reactive functional group comprises a leaving group LG that is an alcohol radical, wherein the alcohol is selected from the group consisting of N-hydroxysuccinimide alcohol, N-hydroxymaleimide, N-hydroxyphthalimide, endo-N-hydroxy-5-norbornene-2,3-dicarboximide and a N-hydroxysulfosuccinimide.

17. The multi-arm tissue-adhesive polymer according to claim 1, wherein n is an integer in the range of 6-8.

18. The multi-arm tissue-adhesive polymer according to claim 1, wherein each arm has a number-average molecular weight in the range of 1-25 kDa.

19. The multi-arm tissue-adhesive polymer according to claim 1, wherein the polymer has molecular weight in the range of 10-80 kDa.

20. The multi-arm tissue-adhesive polymer according to claim 1, wherein the polymer has molecular weight in the range of 20-60 kDa.

* * * * *